United States Patent [19]

Johnson et al.

[11] 4,109,006

[45] Aug. 22, 1978

[54] 1,4-DITHIINOXIDES

[75] Inventors: Richard C. Johnson, Ambler; Peter L. deBenneville, Philadelphia, both of Pa.

[73] Assignee: Warren-Teed Laboratories, Inc., Columbus, Ohio

[21] Appl. No.: 731,154

[22] Filed: Oct. 12, 1976

[51] Int. Cl.$^2$ .................. A61K 31/385; C07D 339/00; C07D 339/02; C07D 339/08

[52] U.S. Cl. .............................. 424/277; 260/327 P; 260/327 M

[58] Field of Search .................... 424/277; 260/327 P, 260/327 M

[56] References Cited

U.S. PATENT DOCUMENTS

| | | | |
|---|---|---|---|
| 2,559,626 | 7/1951 | Jansen | 260/327 M |
| 3,920,438 | 11/1975 | Brewer et al. | 71/73 |

*Primary Examiner*—Frederick E. Waddell
*Attorney, Agent, or Firm*—Marion C. Staves

[57] ABSTRACT

1,4-Dithiinoxides which may be substituted with various radicals, compositions containing said products and methods useful in the treatment of ulcers are disclosed. The products are prepared by oxidation of the correspondingly substituted dithiin.

12 Claims, No Drawings

1,4-DITHIINOXIDES

This invention relates to new chemical compounds which can be described generally as 1,4-dithiinoxides, methods for using same to treat gastric ulcers and methods for their preparation.

Pharmacological studies employing experimental animals indicate that the products of this invention when administered in therapeutic dosages in conventional vehicles are safe and effective antisecretory and antiulcer agents especially useful in treating gastric ulcers.

The 1,4-dithiinoxides of this invention are compounds having the following structural formula:

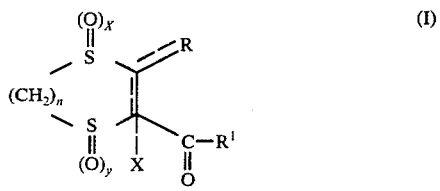

wherein R is hydrogen, alkyl, for example, lower alkyl of from 1 to 8 carbon atoms, such as methyl, ethyl, propyl, iso-propyl, n-butyl, sec-butyl, tert-butyl, pentyl, hexyl, heptyl, octyl and the like; alkylene, for example, lower alkylene, of from 3 to 6 carbon atoms such as allyl and the like; mononuclear aralkyl, for example, mononuclear aryl lower alkyl, such as phenethyl and the like, mononuclear aryl such as phenyl and the like, or cyano; $R^1$ is alkyl, for example, lower alkyl of from 1 to 8 carbon atoms, alkoxy, for example, lower alkoxy of from 1 to 6 carbon atoms such as methoxy, ethoxy, propoxy, butoxy, pentoxy, hexoxy and the like; alkylamino, for example, lower alkylamino of from 1 to 5 carbon atoms, such as methylamino, ethylamino, propylamino, butylamino, pentylamino and the like; di-alkylamino, for example, di-lower alkylamino of from 1 to 5 carbon atoms, such as di-methylamino, di-ethylamino, di-propylamino, di-butylamino, di-pentylamino and the like or mononuclear arylamino, such as phenylamino and the like; X is alkyl, for example, lower alkyl of from 1 to 5 carbon atoms such as methyl, ethyl, propyl, butyl and the like; x and y are the same or different integers having a value of 0 to 2 wherein the sum of x and y is from 1 to 4 and n is an integer of 2 or 3. The dotted line indicates the possibility of a bond.

A preferred embodiment of the invention relates to 2,3-disubstituted-5,6-dihydro-1,4-dithiintetroxides, (Ia, infra) having the following structural formula:

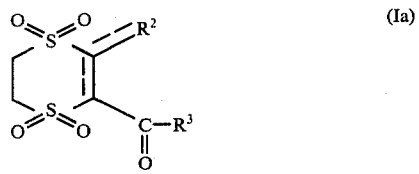

wherein $R^2$ is hydrogen, lower alkyl or cyano and $R^3$ is lower alkoxy, lower alkylamino or di-lower alkylamino.

The 1,4-dithiin-1,1,4,4-tetroxides of this invention (I, supra) are prepared by the oxidation of the corresponding dithiin or of the corresponding dithiin mono-, di- or trioxide (II supra). The oxidation is conducted at a temperature in the range of from 0° to about 90° C. for a period of time of from about 1 hour to about 3 or 4 days but is generally conducted at a temperature in the range of from about 25° to about 50° C. for a period of time from 4 hours to 4 days. Oxidizing agents which can be employed include hydrogen peroxide, and per acids such as m-chloroperbenzoic acid, peracetic acid, performic acid, perphthalic acid, and the like. Solvents which can be employed include chloroform, methylene chloride, acetic acid and the like. Acetic acid is the preferred solvent when hydrogen peroxide is used. The following equation illustrates this reaction:

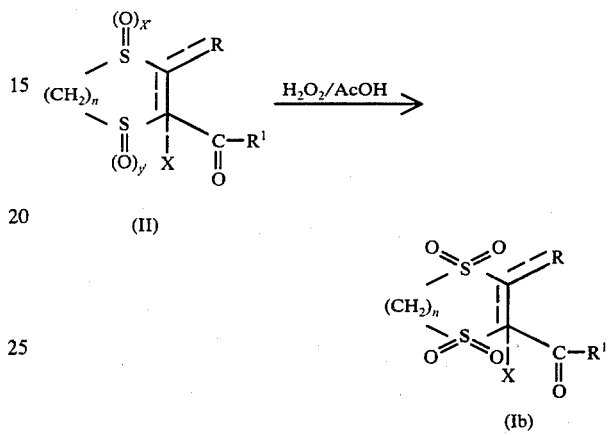

wherein R, $R^1$, X and n are as defined above, $x'$ is an integer of 0–2, $y'$ is an integer of 0–2 and the sum of $x'$ and $y'$ is 0–3.

Those compounds (Ic, infra) wherein the double bond is exo to the dithiin ring may be prepaared by either of two methods. The first method comprises treating a 5,6-dihydrodithiinoxide with dimethylsulfoxide (DMSO) for a period of time of from about 1 to bout 48 hours at a temperature in the range of from 25° to 100° C. The following equation illustrates this process:

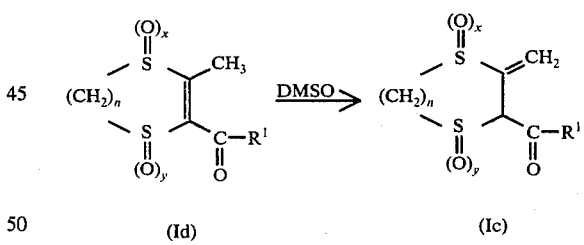

wherein x, y, n and $R^1$ are as defined above.

A second procedure for preparing dithiinoxides (Ie, infra) having an exo double bond comprises treating a 5,6-dihydro-1,4-dithiin with a strong non-nucleophilic base such as lithium diisopropyl amide (LDA), lithiumisopropyl cyclohexylamide, lithium 2,2,6,6-tetramethylpiperidine and the like, followed by treatment with an appropriate halide followed by oxidation as described above to afford the desired product. The following equation illustrates this process:

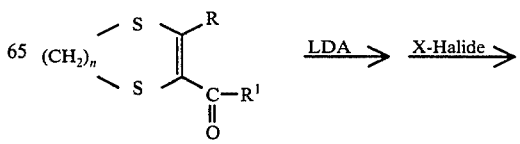

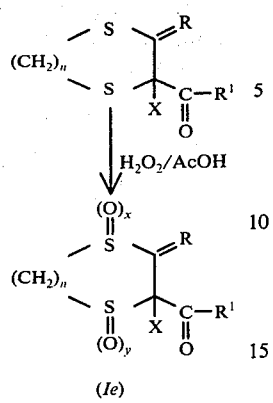

wherein R, R¹, X, x, y, and n are as defined above.

The dithiin mono-, di- or trioxide compounds of Formula II, supra, are also useful as antisecretory and antiulcer agents and are prepared by treating the corresponding 1,4-dithiins with an oxidizing agent such as hydrogen peroxide, sodium periodate, per acids such as m-chloroperbenzoic acid, peracetic, performic, perphthalic and the like. The selection of solvents which may be employed depend upon the nature of the oxidizing agent and include acetic acid, methanol, ethanol, dioxane, chloroform, methylene chloride and the like. The following equation illustrates this process:

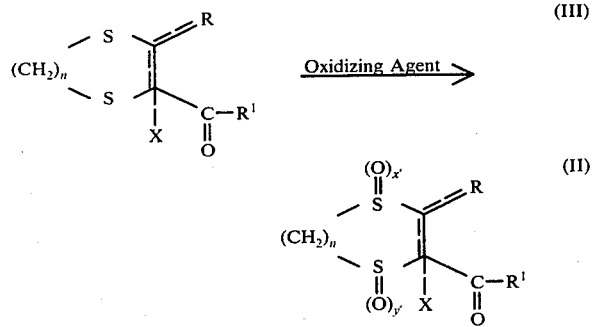

wherein R, R¹, X, x',y' and n are as defined above.

The dithiins and dithiin acids may be prepared by reacting a 1,2-dithiol with a ketone or aldehyde having an α-methylene group or with a β-keto ester followed by halogenation with ring expansion of the dithiolane so produced. This procedure is employed to prepare those compounds wherein R² is alkyl or alkoxy. The following equation illustrates this process:

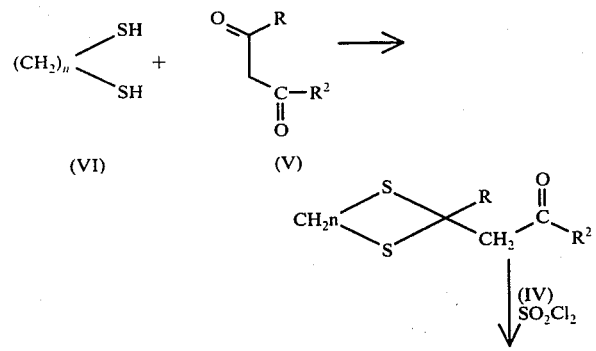

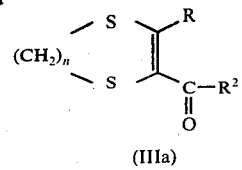

wherein R, X and n are as defined above and R² is alkyl or alkoxy.

Those compounds wherein R¹ in Formula I (supra) is an amino radical are prepared by hydrolyzing an ester to afford an acid followed by treating said acid with an acid halide such as thionyl chloride and the like followed by treatment with an appropriate amine to afford the desired product. The following equation illustrates this process:

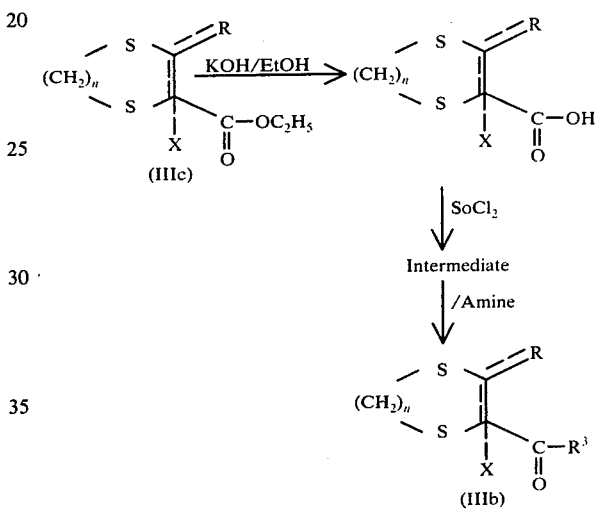

wherein R, X and n are as defined above and R³ is alkylamino, di-alkylamino or arylamino as defined above.

In certain cases, the method of preparation employed leads to a mixture of different isomers. Such isomers may be employed directly or may be resolved into their pure products.

The compositions containing the dithiinoxides as the active ingredient and also the dithiinoxides themselves are antiulcer agents which also includes their use as antisecretory agents which can be administered in a wide variety of therapeutic dosages in conventional vehicles. The products may be administered in a wide variety of pharmaceutically acceptable carriers, for example, in a flavored aqueous solution subdivided into three or four doses per day. It should be noted that when employed in aqueous solutions, the solutions should preferably be neutral or have an acidic pH. Typical formulations contain from about 10 to about 20% of the product in a suitably flavored, colored, thickened, preserved aqueous mixture. The liquid dosage form may contain, in addition to water, small amounts of ethanol or other pharmaceutically acceptable solvent or solvents. Other dosage forms include gels prepared with pectin, agar, hydroxyethyl cellulose or other approved gelling agents, tablets, capsules, pills, which may be microencapsulated, or enterically coated.

In addition, formulations may contain combinations of drugs particularly suited to the healing of ulcers and the relief of ulcer pain, for example, antacids, anticholinergics and the like. Other oral drug combinations are also within the scope of this invention. The oral daily dosage of theproducts may be varied over a wide range of from about 10 mgs. to about 300 mgs./day. The product can be administered in subdivided doses in the form of scored tablets or capsules, however, liquid dosge forms are preferred. These dosage forms permit the symptomatic adjustment of the dosage to the patient to be treated. Effective amount of the drug is ordinarily supplied at a unit dosage level of from about 1 mg. to about 20 mg./kg. of body weight. Preferably, the range is from about 1 mg. to 5 mg./kg. of body weight per day.

The following examples are merely illustrative and should not be construed as limiting the scope of this invention.

EXAMPLE 1

3-Ethoxycarbonyl-2-methyl-5,6-dihydro-1,4-dithiin-1,1,4,4-tetroxide

Step A — 2-Ethoxycarbonylmethyl-2-methyl-1,3-dithiolane

Ethyl acetoacetate (302 g.), ethane-1,2-dithiol (184 ml.), IRA-15 acid resin[1] (5 g.) and benzene (320 ml.) are heated at reflux until the rate of water collection in a Dean-Stark Trap slows (4.5 hrs.). The solution is allowed to cool and the catalyst is removed by filtration. The solvent is removed by distillation and the residual oil is distilled through a simple head at reduced pressure to afford 382 g. (b.p. 94°–95° C./0.6 mm.) of 2-ethoxycarbonylmethyl-2-methyl-1,3-dithiolane
[1]polysulfonic acid Step B — 3-Ethoxycarbonyl-2-methyl-5,6-dihydro-1,4-dithiin Sulfuryl chloride (210 ml.) in solution with methylene chloride (200 ml.) is added with efficient stirring to a solution of 2-ethoxycarbonylmethyl-2-methyl-1,3-dithiolane (512 g.) in methylene chloride (2350 ml.) at such a rate that the temperature does not exceed −70° C. (3.3 hrs.). When the addition is complete, the resulting solution is stirred for one hour at < −65° C. and then allowed to warm to room temperature over 2.5 hours, finally remaining overnight. Gaseous hydrogen chloride begins to be evolved at about −30° C. during the warming process and continues becoming fairly vigorous 0°–10° C. Residual hydrogen chloride is removed by washing with aqueous sodium bicarbonate solution and the product solution is dried over anhydrous sodium sulfate. The solvent is removed by distillation and the residual oil is distilled at reduced pressure to afford 396 g. of 3-ethoxycarbonyl-2-methyl-5,6-dihydro-1,4-dithiin, b.p. 116°–118° C./0.6 mm.

Elemental Analysis for $C_8H_{12}O_2S_2$; Calcd.: C, 47.03; H, 5.92; Found: C, 46.80; H, 5.76.

Step C — 3-Ethoxycarbonyl-2-methyl-5,6-dihydro-1,4-dithiin-1,1,4,4-tetroxide

Hydrogen peroxide (0.10 ml., 35% aqueous solution) as a solution in glacial acetic acid (1.0 ml.) is added dropwise to an ice cooled (10° C.) solution of 3-ethoxycarbonyl-2-methyl-5,6-dihydro-1,4-dithiin (207 mg.) in glacial acetic acid (3.0 ml.) and water (0.5 ml.). The resulting solution is kept at 10° C. or below overnight. Subsequently, an additional quantity of hydrogen peroxide (0.29 ml. — without solvent) is added and the resulting solution is heated on a hot water bath (80° C. but no higher) for one hour. Another quantity of hydrogen peroxide is added (0.20 ml.) and the heating is continued at 50° C. for 0.5 hours. The reaction mixture is concentrated under reduced pressure and the white crystalline product is collected by filtration, washed with methanol and dried to obtain 105 mg. of 3-ethoxycarbonyl-2-methyl-5,6-dihydro-1,4-dithiin-1,1,4,4-tetroxide, m.p. 139°–144° C.

Elemental analysis for $C_8H_{12}O_6S_2$; Calc.: C, 35.81; H, 4.51; Found: C, 36.05; H, 4.54.

EXAMPLE 2

3-Ethoxycarbonyl-2-methylene-1,4-dithiane-1,1,4,4-tetroxide

A solution of 3-ethoxycarbonyl-2-methyl-5,6-dihydro-1,4-dithiin-1,1,4,4-tetroxide (10.0 g.) in dimethyl sulfoxide (50 ml.) is allowed to stand for one week at room temperature. The solution is poured into six volumes of water and the white solid product is collected by filtration and air dried to obtain 9.40 g. of 3-ethoxycarbonyl-2-methylene-1,4-dithiane-1,1,4,4-tetroxide, m.p. 203°–205° C., dec.

Elemental analysis for $C_8H_{12}O_6S_2$; Calc.: C, 35.81; H, 4.51; S, 23.90; Found: C, 35.81; H, 4.53; S, 23.71.

EXAMPLE 3

3-Ethoxycarbonyl-2-(2'-propyl)-5,6-dihydro-1,4-dithiin-1,1,4,4-tetroxide

Step A — 2-Ethoxycarbonylmethyl-2-(2'-propyl)-1,3-dithiolane

By following substantially the procedure of Example 1, Step A, 60 g. of 2-ethoxycarbonylmethyl-2-(2'-propyl)-1,3-dithiolane, b.p. 92° C./0.10 mm. is obtained from ethyl isobutyrylacetate (50 g.) and ethanedithiol (28 ml.).

Elemental analysis for $C_{10}H_{18}O_2S_2$; Calc.: C, 51.27; H, 7.74; S, 27.36; Found: C, 50.99; H, 7.76; S, 27.52.

Step B — 3-Ethoxycarbonyl-2-(2'-propyl)-5,6-dihydro-1,4-dithiin

By following substantially the procedure of Example 1, Step B, 2-ethoxycarbonylmethyl-2-(2'-propyl)-1,3-dithiolane (49 g.) affords 42 g. of 3-ethoxycarbonyl-2-(2'-propyl)-5,6-dihydro-1,4-dithiin, b.p. 114° /0.2 mm).

Elemental analysis for $C_{10}H_{16}O_2S_2$; Calc.: C, 51.69; 6.94; S, 27.60; Found: C, 51.71; H, 7.02; S, 27.84.

Step C — 3-Ethoxycarbonyl-2-(2'-propyl)-5,6-dihydro-1,4-dithiin oxide

A solution of sodium meta-periodate (19.2 g.) in water (180 ml.) is added in one portion with stirring to a solution of 3-ethoxycarbonyl-2-(2'-propyl)-5,6-dihydro-1,4-dithiin (19.7 g.) in methanol (1400 ml.). A solid begins to separate from solution within minutes. When thin layer chromatography indicates an absence of starting material (1–2 hours), the solid is removed by filtration and the filtrate is concentrated under vacuum. The concentrate is diluted with an equal volume of brine and the mixture is extracted with three portions of ethyl acetate. The combined extract is washed with dilute aqueous sodium bisulfite and brine and finally dried over anhydrous sodium sulfate. Removal of solvent under vacuum affords 3-ethoxycarbonyl-2-(2'-propyl)-5,6-dihydro-1,4-dithiin oxide (21.4 g.) as an approximately 9:1 mixture of the 4- and 1-isomers.

Step D — Ethoxycarbonyl-2-(2'-propyl)-5,6-dihydro-1,4-dithiin-1,1,4,4-tetroxide

Hydrogen peroxide (30% aqueous, 25 ml.) is added with stirring to a solution of 3-ethoxycarbonyl-2-(2'-propyl)-5,6-dihydro-1,4-dithiin oxides (21.4 g.) in glacial acetic acid (200 ml.). The solution is placed in a water bath and kept at room temperature until reaction is complete as determined by thin layer chromatography. The solution is poured over ice and the solid product is removed by filtration (15.5 g.). Additional product (4.6 g.) is obtained by extraction of the filtrate with ethyl acetate. The yield of 3-ethoxycarbonyl-2-(2'-propyl)-5,6-dihydro-1,4-dithiin-1,1,4,4-tetroxide is 20.1 g., m.p. from ethyl acetate-heptane, 123°–124° C.

Elemental analysis for $C_{10}H_{16}O_6S_2$; Calc.: C, 40.53; H, 5.44; S, 21.64; Found: C, 40.70; H, 5.53; S, 21.50.

EXAMPLE 4

3-Ethoxycarbonyl-2-n-propyl-5,6-dihydro-1,4-dithiin-4-oxide and
3-Ethoxycarbonyl-2-n-propyl-5,6-dihydro-1,4-dithiin-1-oxide Step A — 2-Ethoxycarbonylmethyl-2-n-propyl-1,3-dithiolane By following substantially the procedure of Example 1, Step A, 273 g. of 2-ethoxycarbonylmethyl-2-n-propyl-1,3-dithiolane, b.p. 87° C./0.07 mm., is obtained from ethyl butyrylacetate (198 g.) and ethanedithiol (120 ml.).

Elemental analysis for $C_{10}H_{18}O_2S_2$; Calc.: C, 51.27; H, 7.74; S, 27.36; Found: C, 50.94; H, 7.76; S, 27.03.

Step B — 3-Ethoxycarbonyl-2-n-propyl-5,6-dihydro-1,4-dithiin

By following substantially the procedure of Example 1, Step B, 2-ethoxycarbonylmethyl-2-n-propyl-1,3-dithiolane (248 g.) affords 212 g. of 3-ethoxycarbonyl-2-n-propyl-5,6-dihydro-1,4-dithiin, b.p. 106° C./0.12 mm.

Elemental analysis for $C_{10}H_{16}O_2S_2$; Calc.: C, 51.69; H, 6.94; S, 27.60; Found: C, 51.60; H, 7.14; S, 27.88.

Step C — 3-Ethoxycarbonyl-2-n-propyl-5,6-dihydro-1,4-dithiin-4-oxide and 3-Ethoxycarbonyl-2-n-propyl-5,6-dihydro-1,4-dithiin-1-oxide By following substantially the procedure of Example 3, Step C, 3-ethoxycarbonyl-2-n-propyl-5,6-dihydro-1,4-dithiin (15.0 g.) yields 16.4 g. of 3-ethoxycarbonyl-2-n-propyl-5,6-dihydro-1,4-dithiin oxide as an approximately 9:1 mixture of the 4- and 1-isomers. The isomers (1.4 g.) are separated by chromatography on silica gel using ethyl acetate-methanol (92:8) as eluant to afford 1.22 g. of 3-ethoxycarbonyl-2-n-propyl-5,6-dihydro-1,4-dithiin-4-oxide ($R_f$ 0.60 on thin layer chromatography using ethyl acetate-methanol (85:15) as developing solvent) and 0.10 g. of ethoxycarbonyl-2-n-propyl-5,6-dihydro-1,4-dithiin-1-oxide ($R_f$ 0.71).

Elemental analysis for the 4-oxide as a partial hydrate — $C_{10}H_{16}S_2O_3$ — 0.188 $H_2O$; Calc.: C, 47.71; H, 6.56; S, 25.47; Found: C, 47.71; H, 6.46; S, 25.57.

Elemental analysis for the 1-oxide — $C_{10}H_{16}S_2O_3$; Calc.: C, 48.36; H, 6.49; S, 25.82; Found: C, 48.14; H, 6.65; S, 25.77.

EXAMPLE 5

3-Ethoxycarbonyl-2-n-propyl-5,6-dihydro-1,4-dithiin-1,1,4,4-tetroxide

By following substantially the procedure of Example 3, Step D, 8.8 g. of 3-ethoxycarbonyl-2-n-propyl-5,6-dihydro-1,4-dithiin-1,1,4,4-tetroxide; m.p. 109°–110° C. is obtained from 3-ethoxycarbonyl-2-n-propyl-5,6-dihydro-1,4-dithiin oxide (10.0 g. of the isomers of Example 4, Step C).

Elemental analysis for $C_{10}H_{16}O_6S_2$; Calc.: C, 40.53; H, 5.44; S, 21.64; Found: C, 40.54; H, 5.63; S, 21.66.

EXAMPLE 6

3-Butoxycarbonyl-2-n-propyl-5,6-dihydro-1,4-dithiin-1,1,4,4-tetroxide

Step A — 3-Butoxycarbonyl-2-n-propyl-5,6-dihydro-1,4-dithiin

A mixture of 3-ethoxycarbonyl-2-n-propyl-5,6-dihydro-1,4-dithiin (20.0 g.), n-butnaol (75 ml., dired over 4A molecular sieves) and sodium hydride (100 mg.; 50% mineral oil dispersion) is heated at 50° C. in an oil bath for one hour. Volatile materials are removed at reduced pressure using an aspirator and the residue is pumped at high vacuum leaving an oil (22.3 g.). Excess base is neutralized with glacial acetic acid. Gas chromatography indicates that the product is present along with starting material in the ratio of 10:1. A portion of the crude product (4.1 g.) is distilled at reduced pressure to afford 3.2 g. of 3-butoxycarbonyl-2-n-propyl-5,6-dihydro-1,4-dithiin, b.p. 116° C./0.10 mm.

Elemental analysis for $C_{12}H_{20}S_2O_3$; Calc.: C, 55.35; H, 7.74; S, 24.62; Found: C, 55.26; H, 7.46; S, 24.37.

Step B — 3-Butoxycarbonyl-2-n-propyl-5,6-dihydro-1,4-dithiin-1,1,4,4-tetroxide

By following substantially the procedure of Example 1, Step C, 3-ethoxycarbonyl-2-n-propyl-5,6-dihydro-1,4-dithiin (9.0 g.) yields 8.15 g. of 3-ethoxycarbonyl-2-n-propyl-5,6-dihydro-1,4-dithiin-1,1,4,4-tetroxide 73.5°–74.5° C.

Elemental analysis for $C_{12}H_{20}O_6S_2$; Calc.: C, 44.43; H, 6.21; S, 19.77; Found: C, 44.69; H, 6.30; S, 19.65.

EXAMPLE 7

3-Hexyloxycarbonyl-2-n-propyl-5,6-dihydro-1,4-dithiin-1,1,4,4-tetroxide

Step A — 3-Hexyloxycarbonyl-2-n-propyl-5,6-dihydro-1,4-dithiin

By following substantially the procedure of Example 6, Step A, 3-ethoxycarbonyl-2-n-propyl-5,6-dihydro-1,4-dithiin (20.0 g.) and anhydrous hexanol (80 ml. dried over 4A molecular sieves) affords 25.1 g. of 3-hexyloxycarbonyl-2l -n-propyl-5,6-dihydro-1,4-dithiin. A portion of the crude product (4.0 g.) is distilled under reduced pressure to afford 3.07 g. of purified product, b.p. 134° C./0.08 mml.

Elemental analysis for $C_{14}H_{24}S_2O_2$; Calc.: C, 58.29; H, 8.39; S, 22.23; Found: C, 58.33; H, 7.99, S, 21.96.

Step B — 3-Hexyloxycarbonyl-2-n-propyl-5,6-dihydro-1,4-dithiin-1,1,4,4-tetroxide By following substantially the procedure of Example 1, Step C, 3-hexyloxycarbonyl-2-n-propyl-5,6-dihydro-1,4-dithiin (21.1 g.) is converted to 23.9 g. 3-hexyloxycarbonyl-2-n-propyl-5,6-dihydro-1,4-dithiin-1,1,4,4-tetroxide, m.p. 87.5°–88.5° C.

Elemental analysis for $C_{14}H_{24}O_6S_2$; Calc.: C, 47.71; H, 6.86; S, 18.19; Found: C, 47.60; H, 6.99; S, 17.95.

EXAMPLE 8

2-Ethoxy-carbonyl-2-methyl-3-methylene-1,4-dithiane-1,1,4,4-tetroxide

Step A — 2-Ethoxycarbonyl-2-methyl-3-methylene-1,4-dithiane

A solution of 3-ethoxycarbonyl-2-methyl-5,6-dihydro-1,4-dithiin (20.4 g.) in anhydrous tetrahydrofuran (20 ml.; distilled from lithium aluminum hydride) is added dropwise under argon with stirring over 0.5 hours to a dry-ice cooled (−70° C.) solution of hexamethylphosphoramide (11 ml.; distilled from sodium hydride) and lithium diisopropylamine [0.11 mole, prepared in situ by addition (<0° C.) of a solution of n-butyl lithium (50.4 ml.; 2.2M) in hexane to a solution of anhydrous diisopropylamine (15.8 ml.; distilled from calcium hydride) in tetrahydrofuran (87 ml.)]. After stirring for one hour at −70° C. a solution of methyl iodide (1.0 ml.) in anhydrous tetrahydrofuran (5 ml.) is added over 0.5 hours so as to maintain the temperature below −60° C. The reaction mixture is stirred for 0.5 hours longer (< −50° C.) and quenched by pouring into a rapidly stirring solution of ammonium sulfate. The organic phase is taken up in ethyl acetate and washed with three portions of water and one portion of brine. After drying over anhydrous sodium sulfate, the solvent is removed and the residual oil distilled under reduced pressure to afford 18.9 g. of 2-ethoxycarbonyl-2-methyl-3-methylene-1,4-dithiane (b.p. 85° C./0.15 mm.).

Elemental analysis for $C_9H_{14}S_2O_2$; Calc.: C, 49.43; H, 6.45; S, 29.34; Found: C, 49.25; H, 6.84; S, 29.34.

Step B — 2-Ethoxycarbonyl-2-methyl-3-methylene-1,4-dithiane-1,4-dioxide

By following substantially the procedure of Example 3, Step C, 2-ethoxycarbonyl-2-methyl-3-methylene-1,4-dithiane (5.12 g.) yields 5.5 g. of 2-ethoxycarbonyl-2-methyl-3-methylene-1,4-dithiane oxide. A portion of this material (4.68 g.) is further converted to 2-ethoxycarbonyl-2-methyl-3-methylene-1,4-dithiane-1,4-dioxide (5.0 g.) following the procedure of Example 3, Step C.

Step C — 2-Ethoxycarbonyl-2-methyl-3-methylene-1,4-dithiane-1,1,4,4-tetroxide

By following substantially the procedure of Example 3, Step D, 2-ethoxycarbonyl-2-methyl-3-methylene-1,4-dithiane-1,4-dioxide (5.0 g.) is converted to 2.8 g. of 2-ethoxycarbonyl-2-methyl-3-methylene-1,4-dithiane-1,1,4,4-tetroxide, m.p. 120°–127° C.

Elemental analysis for $C_9H_{14}O_6S_2$; Calc.: C, 38.29; H, 5.00; S, 22.71; Found: C, 38.45; H, 5.08; S, 22.63.

EXAMPLE 9

3-Ethoxycarbonyl-2-(but-3'-enyl)-5,6-dihydro-1,4-dithiin-1,1,4,4-tetroxide

Step A — 3-Ethoxycarbonyl-2-(but-3'-enyl)-5,6-dihydro-1,4-dithiin

By following substantially the procedure of Example 8, Step A, 3-ethoxycarbonyl-2-methyl-5,6-dihydro-1,4-dithiin (20.4 g.) affords a mixture of 3-ethoxycarbonyl-2-(but-3'-enyl)-5,6-dihydro-1,4-dithiin and 2-ethoxycarbonyl-2-allyl-3-methylene-1,4-dithiane in an approximate ratio of 2:1. Distillation affords 6.7 g. of 3-ethoxycarbonyl-2-(but-3'-enyl)-5,6-dihydro-1,4-dithiin, b.p. 117°–124° C./0.5 mm.

Elemental analysis for $C_{11}H_{16}S_2O_2$; Calc.: C, 54.06; H, 6.60; S, 26.24; Found: C, 54.04; H, 6.39; S, 26.18.

Step B — 3-Ethoxycarbonyl-2-(but-3'-enyl)-5,6-dihydro-1,4-dithiin oxide

By following substantially the procedure of Example 3, Step C, 3-ethoxycarbonyl-2-(but-3'-enyl)-5,6-dihydro-1,4-dithiin (5.34 g.) affords 5.86 g. of 3-ethoxycarbonyl-2-(but-3'-enyl)-5,6-dihydro-1,4-dithiin oxide (mixture of 1- and 4-isomers).

Step C — 3-Ethoxycarbonyl-2-(but-3'-enyl)-5,6-dihydro-1,4-dithiin-1,1,4,4-tetroxide By following substantially the procedure of Example 3, Step D, 3-ethoxycarbonyl-2-(but-3'-enyl)-5,6-dihydro-1,4-dithiin oxide (5.24 g.) affords 3.2 g. of 3-ethoxycarbonyl-2-(but-3'-enyl)-5,6-dihydro-1,4-dithiin-1,1,4,4-tetroxide, m.p. 111.5°–113.0° C.

Elemental analysis for $C_{11}H_{16}O_6S_2$; Calc.: C, 42.84; H, 5.23; S, 20.80; Found: C, 42.77; H, 5.36; S, 20.64.

EXAMPLE 10

2-Methyl-3-phenylcarbamoyl-5,6-dihydro-1,4-dithiin-1,1,4,4-tetroxide

Step A — 2-Carboxy-3-methyl-5,6-dihydro-1,4-dithiin

3-Ethoxycarbonyl-2-methyl-5,6-dihydro-1,4-dithiin (10.0 g.) is heated at reflux for eight hours in a solution of potassium hydroxide (85%; 3.60 g.) in methanol (40 ml.). The cool solution is acidified wth 10% aqueous hydrochloric acid and the precipitate is removed by filtration and dried (8.1 g.). The crude product is recrystallized from ethanol to afford 2-carboxy-3-methyl-5,6-dihydro-1,4-dithiin, m.p. 179°–180° C., dec.

Elemental analysis for $C_6H_8O_2S_2$; Calc.: C, 40.89; H, 4.58; S, 36.38; Found: C, 40.76; H, 4.74; S, 36.32.

Step B — 2-Methyl-3-phenylcarbamoyl-5,6-dihydro-1,4-dithiin

2-Carboxy-3-methyl-5,6-dihydro-1,4-dithiin (7.1 g.), thionyl chloride (4.1 ml.) and benzene (25 ml.) are heated at reflux for two hours. Volatile materials are removed in vacuo (<50° C.) leaving a dark oil. A solution of the oil in methylene chloride (25 ml.) is treated (with stirring) first with triethylamine (8.0 ml.; 2 min.) and then aniline (3.65 g.; 5 min.). After a stirring period of 0.5 hours, the reaction mixture is diluted with methylene chloride, and washed successively with two portions of 10% aqueous hydrochloric acid and one portion of aqueous sodium bicarbonate solution. The dark extract is dried over anhydrous sodium sulfate and stripped of solvent to afford 7.5 g. of 2-methyl-3-phenylcarbamoyl-5,6-dihydro-1,4-dithiin.

Step C — 2-Methyl-3-phenylcarbamoyl-5,6-dihydro-1,4-dithiin-1,1,4,4-tetroxide

By following substantially the procedure of Example 1, Step C, 2-methyl-3-phenylcarbamoyl-5,6-dihydro-1,4-dithiin (7.5 g.) affords 4.35 g. of 2-methyl-3-phenylcarbamoyl-5,6-dihydro-1,4-dithiin-1,1,4-4-tetroxide, m.p. 229° C., dec.

Elemental analysis for $C_{12}H_{13}NO_5S_2$; Calc.: C, 45.7; H, 4.16; H, 4.44; S, 20.33; Found C, 45.44; H, 4.32; N, 4.28; S, 20.40.

EXAMPLE 11

2-Ethylcarbamoyl-3-n-propyl-5,6-dihydro-1,4-dithiin-1,1,4-4-tetroxide

Step A — 2-Carboxy-3-n-propyl-5,6-dihydro-1,4-dithiin

By following substantially the procedure of Example 10, Step A, except using ethanol as the solvent, 3-ethoxycarbonyl-2-n-propyl-5,6-dihydro-1,4-dithiin (100 g.), there is obtained after two hours of reflux 87.0 g. of 2-carboxy-3-n-propyl-5,6-dihydro-1,4-dithiin, m.p. 105°–108° C.

Elemental analysis for $C_8H_{12}O_2S_2$; Calc.: C, 47.03; H, 5.92; S, 31.39; Found: C, 46.96; H, 5.91; S, 31.41.

Step B — 2-Ethylcarbamoyl-3-n-propyl-5,6-dihydro-1,4-dithiin

An ice-cooled solution (5° C.) of 2-carboxy-3-n-propyl-5,6-dihydro-1,4-dithiin (10.0 g.) in anhydrous tetrahydrofuran (120 ml.); distilled from lithium aluminum hydride) is stirred first with anhydrous triethylamine (5.43 g.; distilled from calcium hydride added by drops over 2 min.) and subsequently with ethyl chloroformate (5.3 g.; added by drops over 15 min., 7° C.). The mixture was stirred for 10 min. and 3.7 g. of 70% aqueous ethyl amine was added by drops over 15 min. (<70° C.). The final mixture was allowed to warm to room temperature (1 hour) and is stirred for two hours longer before pouring into a solution of excess ammonium sulfate. The organic phase is taken up in ethyl acetate and washed with aqueous sodium bicarbonate (2 portions) and brine (1 portion). After drying over anhydrous sodium sulfate, solvent is removed leaving 8.21 g. of 2-ethylcarbamoyl-3-n-propyl-5,6-dihydro-1,4-dithiin, m.p. 97.0°–98.5° C.

Elemental analysis for $C_{10}H_{17}NOS_2$; Calc.: C, 51.9; H, 7.41; N, 6.05; S, 27.72; Found: C, 52.00; H, 7.58; N, 5.99; S, 27.27.

Step C — 2-Ethylcarbamoyl-3-n-propyl-5,6-dihydro-1,4-dithiin oxide

By following substantially the procedure of Example 3, Step C, 2-ethylcarbamoyl-3-n-propyl-5,6-dihydro-1,4-dithiin (4.78 g.) yields 5.12 g. of 2-ethylcarbamoyl-3-n-propyl-5,6-dihydro-1,4-dithiin oxide.

Step D — 2-Ethylcarbamoyl-3-n-propyl-5,6-dihydro-1,4-dithiin-1,1,4,4-tetroxide

By following substantially the procedure of Example 3, Step D, 2-ethylcarbamoyl-3-n-propyl-5,6-dihydro-1,4-dithiin oxide (4.09 g.) yields 4.46 g. of 2-ethylcarbamoyl-3-n-propyl-5,6-dihydro-1,4-dithiin-1,1,4,4-tetroxide, m.p. 204.5°–205.5° C.

Elemental analysis for $C_{10}H_{17}NO_5S_2$; Calc.: C, 40.66; H, 5.80; N, 4.74; S, 21.71; Found: C, 41.03; H, 5.89; N, 4.73; S, 22.22.

EXAMPLE 12

2-n-Pentylcarbamoyl-3-n-propyl-5,6-dihydro-1,4-dithiin-1,1,4,4-tetroxide

Step A — 2-n-Pentylcarbamoyl-3-n-propyl-5,6-dihydro-1,4-dithiin

By following substantially the procedure of Example 11, Step B, 2-carboxy-3-n-propyl-5,6-dihydro-1,4-dithiin (10.0 g.) yields 7.91 g. of 2-n-pentylcarbamoyl-3-n-propyl-5,6-dihydro-1,4-dithiin, m.p. 88.5°–90.0° C.

Elemental analysis for $C_{13}H_{23}NOS_2$; Calc.: C, 57.10; H, 8.48; N, 5.12; S, 23.45; Found C, 57.48; H, 9.00; N, 5.11; S, 23.23.

Step B — 2-n-Pentylcarbamoyl-3-n-propyl-5,6-dihydro-1,4-dithiin oxide

By following substantially the procedure of Example 3, Step C, 2-n-pentylcarbamoyl-3-n-propyl-5,6-dihydro-1,4-dithiin (5.0 g.) yields 5.29 g. of 2-n-pentylcarbamoyl-3-n-propyl-5,6-dihydro-1,4-dithiin oxide as a mixture of the 1- and 4-isomers.

Step C — 2-n-Pentylcarbamoyl-3-n-propyl-5,6-dihydro-1,4-dithiane-1,1,4,4-tetroxide By following substantially the procedure of Example 3, Step D, 2-n-pentylcarbamoyl-3-n-propyl-5,6-dihydro-1,4-dithiin oxides (4.43 g.) yields 4.12 g. of 2-n-pentylcarbamoyl-3-n-propyl-5,6-dihydro-1,4-dithiin-1,1,4,4-tetroxide, m.p. 182°–182.5° C.

Elemental analysis for $C_{13}H_{23}NO_5S_2$; Calc.: C, 46.27; H, 6.87; N, 4.15; S, 19.00; Found: C, 46.68; H, 6.92; N, 4.39; S, 18.51.

EXAMPLE 13

2-Diethylcarbamoyl-3-n-propyl-5,6-dihydro-1,4-dithiin-1,1,4,4-tetroxide

Step A — 2-Diethylcarbamoyl-3-n-propyl-5,6-dihydro-1,4-dithiin

By following substantially the procedure of Example 11, Step B, 2-carboxy-3-n-propyl-5,6-dihydro-1,4-dithiin (10.0 g.) yields 3.05 g. of 2-diethylcarbamoyl-3-n-propyl-5,6-dihydro-1,4-dithiin, b.p. 130°–132° C./0.05 mm.

Step B — 2-Diethylcarbamoyl-3-n-propyl-5,6-dihydro-1,4-dithiin oxide

By following substantially the procedure of Example 3, Step C, 2-diethylcarbamoyl-3-n-propyl-5,6-dihydro-1,4-dithiin (2.06 g.) yields 2.20 g. of 2-diethylcarbamoyl-3-n-propyl-5,6-dihydro-1,4-dithiin oxide.

Step C — 2-Diethylcarbamoyl-3-n-propyl-5,6-dihydro-1,4-dithiin-1,1,4,4-tetroxide By following substantially the procedure of Example 3, Step D, 2-diethylcarbamoyl-3-n-propyl-5,6-dihydro-1,4-dithiin oxide (2.10 g.) yields 1.9 g. of 2-diethylcarbamoyl-3-n-propyl-5,6-dihydro-1,4-dithiin-1,1,4,4-tetroxide, m.p. 180.5°–181.5° C.

Elemental analysis for $C_{12}H_{21}NO_5S_2$; Calc.: C, 44.56; H, 6.54; N, 4.33; S, 19.83; Found: C, 44.39; H, 6.51; N, 4.61; S, 19.73.

EXAMPLE 14

2-Cyano-3-methoxycarbonyl-5,6-dihydro-1,4-dithiin-1- and 4-oxides

Step A — Methyl 2-cyano-2,2-dichloropropionate

Methyl-2-cyanopropionate (452.0 g.) is added with stirring to sulfuryl chloride (1188.0 g.) containing anhydrous zinc chloride (3.45 g.). The solution is stirred slowly in a dimly lighted place while being protected from moisture. Gas evolution is slow initially but becomes sufficiently vigorous after 6–10 hours to lift an average sized drying tube. (Care is advised). Stirring is continued until gas evolution becomes slow (7–10 days). Excess sulfuryl chloride is removed using an aspirator taking care to keep the reaction mixture dry. Distillation affords 476.0 g. of methyl 2-cyano-2,2-dichloropropionate, b.p. 45° C./0.1 mm.

Elemental analysis for $C_5H_5NCl_2O_2$; Calc.: C, 33.00; H, 2.77; N, 7.70; Cl, 38.96; Found: C, 33.57; H, 2,80; N, 7.62; Cl, 38.46.

Step B — Methyl 2-chloro-2-cyanoacrylate

Methyl 2-cyano-2,2-dichloropropionate (421 g.) and benzene (1.05 l.) are cooled in an ice bath to 12° C. Triethylamine added with stirring at such a rate that the temperature does not exceed 17° C. Addition of triethylamine is continued until starting material is no longer detected by gas chromatography. (A total of 275 ml. of triethylamine is required.) Solid is removed by filtration and the filter cake is washed with benzene (1.0 l.). The filtrate is concentrated by distillation of solvent through a 40 cm. Vigreux column using an aspirator. The residual oil is distilled at reduced pressure affording 326.0 g. of methyl 2-chloro-2-cyanoacrylate, b.p. 65° C/1.5 mm. as a 9:1 mixture of geometric isomers.

Step C — Trans-2-cyano-3-methoxycarbonyl-1,4-dithiane

A solution of methyl 2-chloro-2-cyanoacrylate (110 g.) in methylene chloride (250 ml.) is added dropwise (2.5 hrs.) with efficient stirring to a cooled solution (15° C.) of ethane-1,2-dithiol (62 ml.) and triethylamine (105 ml.) in methylene chloride (2.8 l.). The solution is stirred for 0.5 hours longer and subsequently washed with a portion each of two percent aqueous hydrochloric acid and water. The crude product solution is dried over anhydrous sodium sulfate. Solvent is removed by distillation and the residual oil is distilled at reduced pressure. Early fractions contained mixtures of isomeric 2-cyano-2-methoxycarbonylmethyl-1,3-dithiolane and 2-cyanomethyl-2-methoxycarbonyl-1,3-dithiolane (72 g., b.p. 140°–147° C./0.25 mm.). The last fraction (13.4 g., b.p. 147°–155° C./0.25 mm.) contained the aforementioned materials (75%) along with trans-2-cyano-3-methoxycarbonyl-1,4-dithiane (25%). The latter crystallized from the mixture on standing and was removed by filtration and washed with ether to afford 1.96 g. of trans-2-cyano-3-methoxycarbonyl-1,4-dithiane, m.p. 114.5°–116.0° C.

Elemental analysis for $C_7H_9NO_2S_2$; Calc.: C, 41.36; H, 4.46; N, 6.89; S, 31.55; Found: C, 41.05; H, 4.39; N, 6.92; S, 31.12.

Step D —2-Cyano-3-methoxycarbonyl-5,6-dihydro-1,4-dithiin

Trans-2-cyano-3-methoxycarbonyl-1,4-dithiane (1.01 g.) is treated with sulfuryl chloride (0.71 g.) using the conditions and procedure of Example 1, Step B. The solution of product obtained after processing using aqueous sodium bicarbonate solution is treated with an excess of triethylamine (1.0 ml.). After standing for 0.5 hr., the mixture is washed with one portion each of water, 10% aqueous hydrochloric acid and water. After drying over anhydrous sodium sulfate, the solvent is removed to afford 0.95 g. of 2-cyano-3-methoxycarbonyl-5,6-dihydro-1,4-dithiin, m.p. 91.0°–92.5° C.

Elemental analysis for $C_7H_7NO_2S_2$; Calc.: C, 41.77; H, 3.51; N, 6.96; S, 31.86; Found: C, 41.44; H, 3.23; N, 6.86; S, 31.42.

Step E — 2-Cyano-3-methoxycarbonyl-5,6-dihydro-1,4-dithiin 1-, and 4-oxides

An ice cooled solution of 2-cyano-3-methoxycarbonyl-5,6-dihydro-1,4-dithiin (0.257 g.) in methylene chloride (25 ml.) is treated (addition dropwise with stirring over 15 minutes) with a solution of metachloroperbenzoic acid (0.260 g.) in methylene chloride (10 ml.). The solution is stirred for 15 minutes longer and subsequently washed with aqueous sodium bicarbonate solution containing a small amount of sodium bisulfite. After drying over anhydrous sodium sulfate, solvent is removed to afford 0.28 g. of a 1:2 mixture of 2-cyano-3-methoxycarbonyl-5,6-dihydro-1,4-dithiin 1-, and 4-oxides.

EXAMPLE 15

3-Ethoxycarbonyl-2-methyl-5,6-dihydro-1,4-dithiin-4-oxide

Following the procedure of Example 3, Step C, 3-ethoxycarbonyl-2-methyl-5,6-dihydro-1,4-dithiin (2.04 g.) gave a 1:10 mixture of 3-ethoxycarbonyl-2-methyl-5,6-dihydro-1,4-dithiin 1-, and 4-oxides (2.25 g.). Following the procedure of Example 4, Step C, 1.12 g. of the mixture is separated on chromatography giving 3-ethoxycarbonyl-2-methyl-5,6-dihydro-1,4-dithiin-4-oxide [0.985 g, $R_f$ 0.60 on thin layer chromatography using ethyl acetate-methanol (85.15) as developing solvent] and 3-ethoxycarbonyl-2-methyl-5,6-dihydro-1,4-dithiin-1-oxide (0.102 g., $R_f$ 0.71).

Elemental analysis for $C_8H_{12}O_3S_2.0.145\ H_2O$; Calc.: C, 43.10; H, 5.56; S, 28.77; O, Found (4-oxide) C, 43.10; H, 5.99; S, 27.48; O, 21.62.

EXAMPLE 16

3-Ethoxycarbonyl-2-methyl-5,6-dihydro-1,4-dithiin-1,4,4-trioxide

The procedure of Example 3, Step D, is followed except that the reaction is stopped at a point when thin layer chromotography indicates an incomplete transformation to the corresponding tetroxide. Thus the chromatogram [ethyl acetate-carbon tetrachloride (1:1)] of the reaction mixture shows two principle spots ($R_f$ 0.8, tetroxide and $R_f$ 0.3, trioxide). A portion of the product mixture so obtained (10.0 g.) is taken up in a minimum volume of methylene chloride and passed through Bio Sil A (50 g.). Continued elution with methylene chloride yields 5.19 g. of essentially pure tetroxide. Elution with ethyl acetate affords 3.8 g. of 3-ethoxycarbonyl-2-methyl-5,6-dihydro-1,4-dithiin-1,4,4-trioxide, m.p. 138°–140° C.

Elemental analysis for $C_8H_{12}O_5S_2$; Calc.: C, 38.08; H, 4.79; S, 25.42; Found: C, 38.16; H, 4.87; S, 25.43.

EXAMPLE 17

2-tert-Butyl-3-ethoxycarbonyl-5,6-dihydro-1,4-dithiin-1,1,4,4-tetroxide

Step A — 2-tert-Butyl-2-ethoxycarbonylmethyl-1,3-dithiolane

Following substantially the procedure of Eliel and Hartmann (J. Org. Chem. 37, 506 (1972)) for the preparation of ethyl 1,3-dithiane-2- carboxylate and by substituting ethyl pivaloylacetate (20.0 g.) and ethane-1,2-dithiol (10.9 g.), there is obtained 15.8 g. of 2-tert-butyl-2-ethoxycarbonylmethyl-1,3-dithiolane, b.p. 100° C/0.10 mm.

Step B — 2-tert-butyl-3-ethoxycarbonyl-5,6-dihydro-1,4-dithiin

By following substantially the procedure of Example 1, Step B, 2-tert-butyl-2-ethoxycarbonylmethyl-1,3-dithiolane (14.4 g.) yields 9.83 g. of 2-tert-butyl-3-ethoxycarbonyl-5,6-dihydro-1,4-dithiin, b.p. 109°–111° C./0.08 mm.

Step C — 2-tert-Butyl-3-ethoxycarbonyl-5,6-dihydro-1,4-dithiin-1,1,4,4-tetroxide By following substantially the procedure of Example 1, Step C, 2-tert-butyl-3-ethoxycarbonyl-5,6-dihydro-1,4-dithiin (5.00 g.) yields 4.03 g. of 2-tert-butyl-3-ethoxycarbonyl-5,6-dihydro-1,4-dithiin-1,1,4,4-tetroxide, m.p. 133.0°–134.0° C.

Elemental analysis for $C_{11}H_{18}O_6S_2$; Calc.: C, 42.57; H, 5.85; S, 20.66; Found: C, 42.81; H, 6.20; S, 20.42.

EXAMPLE 18

2-Ethyl-3-ethoxycarbonyl-5,6dihydro-1,4-dithiin-1,1,4,4-tetroxide

Step A — 2-Ethyl-2-ethoxycarbonylmethyl-1,3-dithiolane

By following substantially the procedure of Example 17, Step A, ethyl propionylacetate (29.6 g.) yields 32.2 g. of 2-ethyl-2-ethoxycarbonylmethyl-1,3-dithiolane, b.p. 88°–89° C./0.15 mm.

Elemental analysis for $C_9H_{16}O_2S_2$; Calc.: C, 49.06; H, 7.32; S, 29.10; Found: C, 48.80; H, 7.79; S, 29.58.

Step B — 2-Ethyl-3-ethoxycarbonyl-5,6-dihydro-1,4dithiin

By following substantially the procedure of Example 1, Step B, 2-ethyl-2-ethoxycarbonylmethyl-1,3-dithiolane (28.0 g.) yields 21.7 g. of 2-ethyl-3-ethoxycarbonyl-5,6-dihydro-1,4-dithiin, b.p. 126°–128° C./0.25 mm.

Elemental analysis for $C_9H_{14}O_2S_2$; Calc.: C, 49.51; H, 6.46; S, 29.37; Found: C, 49.08; H, 6.57; S, 29.17.

Step C — 2-Ethyl-3-ethoxycarbonyl-5,6-dihydro-1,4-dithiin-1,1,4,4-tetroxide

By following substantially the procedure of Example 1, Step C, 2-ethyl-3-ethoxycarbonyl-5,6-dihydro-1,4-dithiin (10.0 g.) yields 4.86 g. of 2-ethyl-3-ethoxycarbonyl-5,6-dihydro-1,4-dithiin-1,1,4,4-tetroxide, m.p. 132.0°–133.5° C.

Elemental analysis for $C_9H_{14}O_6S_2$; Calc.: C, 38.59; H, 5.00; S, 22.71; Found: C, 38.52; H, 5.20; S, 23.01.

EXAMPLE 19

2-Ethoxycarbonyl-3-n-pentyl-5,6-dihydro-1,4-dithiin-1,1,4,4-tetroxide

Step A — Ethyl 3oxooctanoate

By following substantially the procedure described by Huckin and Weiler, (J. Am. Chem. Soc., 96, 1082 (1974), ethyl acetoacetate (25.0 g.) and n-butyl bromide (25.0 ml.) yields 15.1 g. of ethyl 3-oxooctoanoate, b.p. 86° C/1.4 mm.

Step B — 2-n-Pentyl-2-ethoxycarbonylmethyl-1,3-dithiolane

By following substantially the procedure of Example 1, Step A, ethyl 3-oxooctanoate (14.0 g.) yields 11.0 g. of 2-n-pentyl-2-ethoxycarbonylmethyl-1,3-dithiolane, b.p. 111°–116° C./0.08 mm.

Elemental analysis for $C_{12}H_{22}O_2S_2$; Calc.: C, 54.92; H, 8.45; S, 24.44; Found: C, 55.13; H, 8.64; S, 24.95.

Step C — 2-Ethoxycarbonyl-3-n-pentyl-5,6-dihydro-1,4-dithiin

By following substantially the procedure of Example 1, Step B, 2-n-pentyl-2-ethoxycarbonylmethyl-1,3-dithiolane (12.9 g.) yields 8.33 g. of 2-ethoxycarbonyl-3-n-pentyl-5,6-dihydro-1,4dithiin, b.p. 145° C./0.2 mm.

Elemental analysis for $C_{12}H_{20}O_2S_2$; Calc.: C, 55.35; H, 7.74; S, 24.62; Found: C, 55.55; H, 7.94; S, 25.01.

Step D — 2-Ethoxycarbonyl-3-n-pentyl-5,6-dihydro-1,4-dithiin-1,1,4,4-tetroxide

By following substantially the procedure of Example 1, Step C, 2-ethoxycarbonyl-3-n-pentyl-5,6-dihydro-1,4-dithiin (5.00 g.) yields 2.9 g. of 2-ethoxycarbonyl-3-n-pentyl-5,6-dihydro-1,4-dithiin-1,1,4,4-tetroxide, m.p. 106.5°–108.5° C.

Elemental analysis for $C_{12}H_{20}O_6S_2$; Calc.: C, 44.43; H, 6.21; S, 19.77; Found: C, 44.82; H, 6.53; S, 20.00.

EXAMPLE 20

2-Ethoxycarbonyl-3-n-octyl-5,6-dihydro-1,4-dithiin-1,1,4,4-tetroxide

Step A — Ethyl 3-oxoundecanoate

By following substantially the procedure of Example 19, Step A, ethyl acetoacetate (25.4 g.) and n-heptyl bromide (39.8 g.) yields 21.9 g. of ethyl-3-oxoundecanoate, b.p. 116° C/0.6 mm.

Step B — 2-Ethoxycarbonylmethyl-2-n-octyl-1,3-dithiolane

By following substantially the procedure of Example 1, Step A, ethyl-3-oxoundecanoate (16.7 g.) yields 9.2 g. of 2-ethoxycarbonylmethyl-2-n-octyl-1,3-dithiolane, b.p. 140°–145° C./0.1 mm.

Elemental analysis for $C_{15}H_{28}O_2S_2$; Calc.: C, 59.16; H, 9.27; S, 21.06; Found: C, 59.96; H, 9.15; S, 20.13.

Step C — 2-Ethoxycarbonyl-3-n-octyl-5,6-dihydro-1,4-dithiin

By following substantially the procedure of Example 1, Step B, 2-ethoxycarbonylmethyl-2n-octyl-1,3-dithiolane (10.9 g.) yields 6.28 g. of 2-ethoxycarbonyl-3-n-octyl-5,6-dihydro-1,4-dithiin, b.p/166°–173° C./0.08 mm.

Elemental analysis for $C_{15}H_{26}O_2S_2$; Calc.: C, 59.56; H, 8.66; S, 21.10; Found: C, 59.21; H, 8.72; S, 20.60.

Step D — 2-Ethoxycarbonyl-3-n-octyl-5,6-dihydro-1,4-dithiin-1,1,4,4-tetroxide

By following substantially the procedure of Example 1, Step C, 2-ethoxycarbonyl-3-n-octyl-5,6-dihydro-1,4-dithiin (3.00 g.) yields 2.56 g. of 2-ethoxycarbonyl-3-n-octyl-5,6-dihydro-1,4-dithiin-1,1,4,4-tetroxide, m.p. 104.5°–106.5° C.

Elemental analysis for $C_{15}H_{26}O_6S_2$; Calc.: C, 49.16; H, 7.15; S, 17.50; Found: C, 49.50; H, 7.56; S, 17.63.

EXAMPLE 21

2-Ethoxycarbonyl-3-(2'-phenethyl)-5,6-dihydro-1,4-dithiin-1,1,4,4-tetroxide

Step A — Ethyl 3-oxo-5-phenylpentanoate

By following substantially the procedure of Example 19, Step A, ethyl acetoacetate (25.3 g.) and benzyl chloride (34.8 g.) yields 30.0 g. of ethyl 3-oxo-5-phenylpentanoate, b.p. 123° C./0.4 mm.

Step B — 2-Ethoxycarbonylmethyl-2-(2'-phenethyl)-1,3-dithiolane

By following substantially the procedure of Example 1, Step A, ethyl 3-oxo-5-phenylpentanoate (22.0 g.) yields 18.2 g. of 2-ethoxycarbonylmethyl-2-(2'-phenethyl)-1,3-dithiolane, b.p. 140°–148° C./0.03 mm.

Step C — 2-Ethoxycarbonyl-3-(2'-phenethyl)-5,6-dihydro-1,4-dithiin

By following substantially the procedure of Example 1, Step B, 2-ethoxycarbonylmethyl-2-(2'-phenethyl)-1,3-dithiolane (19.8 g.) yields 10.2 g. of 2-ethoxycarbonyl-3-(2'-phenethyl)-5,6-dihydro-1,4-dithiin, b.p. 178°–185° C./0.20 mm.

Elemental analysis for $C_{15}H_{18}O_2S_2$; Calc.: C, 61.19; H, 6.16; S, 21.78; Found: C, 61.67; H, 5.99; S, 21.77.

Step D — 2-Ethoxycarbonyl-3-(2'-phenethyl)-5,6-dihydro-1,4-dithiin-1,1,4,4-tetroxide By following substantially the procedure of Example 1, Step C, 2-ethoxycarbonyl-3-(2'-phenethyl)-5,6-dihydro-1,4-dithiin (10.0 g.) yields 4.81 g. of 2-ethoxycarbonyl-3-(2'-phenethyl)-5,6-dihydro-1,4-dithiin-1,1,4,4-tetroxide, m.p. 127.5°–129.0° C.

Elemental analysis for $C_{15}H_{18}O_6S_2$; Calc.: C, 50.20; H, 5.06; S, 17.89; Found: C, 50.54; H, 5.33; S, 18.16.

EXAMPLE 22

2-Acetyl-3-methyl-5,6-dihydro-1,4-dithiin

Step A — 2-Methyl-2-(2'-oxopropyl)-1,3di-thiolane

By following substantially the procedure of Example 1, Step A, pentane-2,4-dione (100 g.) yields 144 g. of 2-methyl-2-(2'-oxopropyl)-1,3-dithiolane, b.p. 80° C./0.05 mm.

Elemental analysis for $C_7H_{12}OS_2$; Calc.: C, 47.69; H, 6.86; S, 36.37; Found: C, 48.13; H, 7.11; S, 36.05.

Step B — 2-Acetyl-3-methyl-5,6-dihydro-1,4-dithiin

By following substantially the procedure of Example 1, Step B, 2-methyl-2-(2'-oxopropyl)-1,3-dithiolane (50.9 g.) yields 23.1 g. of 2-acetyl-3-methyl-5,6-dihydro-1,4-dithiin, b.p. 94°–95° C./0.05 mm.

Elemental analysis for $C_7H_{10}OS_2$; Calc.: C, 48.24; H, 5.78; S, 36.79; Found: C, 48.23; H, 6.17; S, 36.84.

EXAMPLE 23

2-Ethoxycarbonyl-5,6-dihydr-1,4-dithiin 4-oxide

Step A — 2-EThoxycarbonyl-5,6-dihydro-1,4-dithiin

Ethyl bromopyruvate (87.2 g) is added with stirring to a solution of ethane-1,2-dithiol in benzene (475 ml.). Aqueous hydrogen bromide soon begins to separate out as a phase. The mixture is allowed to stand overnight. The aqueous phase is separated and the organic phase washed with aqueous sodium bicarbonate solution with final drying over anhydrous sodium sulfate. Solvent is removed and the product distilled under reduced pressure to afford 67.3 g. of 2-ethoxycarbonyl-5,6-dihydro-1,4-dithiin, b.p. 106° C/0.09 mm.

Elemental analysis for $C_7H_{10}O_2S_2$; Calc.: C, 44.18; H, 5.30; S, 33.70; Found: C, 43.92; H, 5.32; S, 33.46.

Step B — 2-Ethoxycarbonyl-5,6-dihydro-1,4-dithiin 4-, and 1-oxides

By following substantially the procedure of Example 3, Step C, 2-ethoxycarbonyl-5,6-dihydro-1,4-dithiin (15.0 g.) yields a 1:10 mixture of 2-ethoxycarbonyl-5,6-dihydro-1,4-dithiin 4-, and 1-oxides. A sample of the mixture is chromotographed (1.50 g.) on silica gel according to the procedure of Example 4, Step C, to afford 1.02 g. of 2-ethoxycarbonyl-5,6-dihydro1,4-dithiin-1-oxide [$R_f$ 0.55 on thin layer chromatography using ethyl acetate-methanol (85:15) as developing solvent] and 0.086 g. of 2-ethoxycarbonyl-5,6-dihydro-1,4-dithiin-4-oxide ($R_f$ 0.65). The 1-oxide was sent for analysis.

Elemental analysis for $C_7H_{10}O_3S_2 \cdot 0.317$ $H_2O$; Calc.: C, 39.66; H, 5.06; S, 30.25; Found: C, 39.66; H, 5.32; S, 30.46.

EXAMPLE 24

2-Ethoxycarbonyl-3-methyl 1,4-dithiacyclohept-2-ene-1,1,4,4-tetroxide

Step A — 2-Ethoxycarbonylmethyl-2-methyl-1,3-dithiane

By following substantially the procedure of Example 1, Step A, ethyl acetoacetate (60.8 g.) and propane-1,3-dithiol (47 ml.) yields 91.2 g. of 2-ethoxycarbonylmethyl-2-methyl-1,3-dithiane, b.p. 83° C./0.02 mm.

Elemental analysis for $C_9H_{16}O_2S_2$; Calc.: C, 49.06; H, 7.32; S, 29.10; Found: C, 49.00; H, 7.21; S, 28.91.

Step B — 2-Ethoxycarbonyl-3-methyl-1,4-dithiacylcohept-2-ene

By following substantially the procedure of Example 1, Step B, 2-ethoxycarbonylmethyl-2-methyl-1,3-dithiane (59.9 g.) yields 8.0 g. of 2-ethoxycarbonyl-3-methyl-1,4-dithiacyclohept-2-ene, b.p. 130° C./0.2 mm.

Elemental analysis for $C_9H_{14}O_2S_2$; Calc.: C, 49.51; H, 6.46; S, 29.37; Found: C, 49.26; H, 6.83; S, 28.90.

Step C — 2-Ethoxycarbonyl-3-methyl-1,4-dithiacyclohept-2-ene oxide

By following substantially the procedure of Example 3, Step C, 2-ethoxycarbonyl-3-methyl-1,4-dithiacyclohept-2-ene (3.25 g.) yields 3.44 g. of 2-ethoxycarbonyl-3-methyl-1,4-dithiacyclohept-2-ene oxide.

Step D — 2-Ethoxycarbonyl-3-methyl-1,4-dithiacyclohept-2-ene-1,1,4,4-tetroxide

By following substantially the procedure of Example 3, Step D, 3-ethoxycarbonyl-2-methyl-1,4-dithiacyclohept-2-end oxide (3.22 g.) yields 3.13 g. of 2-ethoxycarbonyl-3-methyl-1,4-dithiacyclohept-2-ene-1,1,4,4-tetroxide, m.p. 125°–126° C.

Elemental analysis for $C_9H_{14}O_6S_2$; Calc.: C, 38.29; H, 5.00; S, 22.71; Found: C, 37.91; H, 4.99; S, 22.19.

EXAMPLE 25

2-Ethoxycarbonyl-3-(2'-propyl)-1,4-dithiacyclohept-2-ene-1,1,4,4-tetroxide

Step A — 2-Ethoxycarbonylmethyl-2-(2'-propyl)-1,3-dithiane

By following substantially the procedure of Example 1, Step A, ethyl acetoacetate (45.0 g.) and propane-1,3-diethiol (29 ml.) yields 62.5 g. of 2-ethoxycarbonylmethyl-2-(2'-propyl)-1,3-dithiane, b.p. 109° C./0.02 mm.

Elemental analysis for $C_{11}H_{20}O_2S_2$; Calc.: C, 53.19; H, 8.12; S, 25.82; Found: C, 53.14; H, 8.23; S, 25.65.

Step B — 2-Ethoxycarbonyl-3-(2'-propyl)-1,4-dithiacyclohept-2-ene

By following substantially the procedure of Example 1, Step B, 2-ethoxycarbonylmethyl-2-(2'-propyl)-1,3-dithiane (45.0 g.) yields 13.2 g. of 2-ethoxycarbonyl-3-(2'-propyl)-1,4-dithiacyclohept-2-ene, b.p. 145° C./0.35 mm. The product contains ~50% of the tautomeric-2-ethoxycarbonyl-3-(2'-propylidene)-1,4-dithiacycloheptane.

Elemental analysis for $C_{11}H_{18}O_2S_2$; Calc.: C, 53.62; H, 7.36; S, 26.03; Found: C, 53.63; H, 7.59; S, 26.23.

Step C — 2-Ethoxycarbonyl-3-(2'-propyl)-1,4-dithiacyclohept-2-ene-oxide

By following substantially the procedure of Example 3, Step C, 2-ethoxycarbonyl-3-(2'-propyl)-1,4-dithiacyclohept-2-ene (5.91 g. as a 50% mixture with its tautometer) yields 6.3 g. of 2-ethoxycarbonyl-3-(2'-propyl)-1,4-dithiacyclohept-2-ene oxide.

Step D — 2-Ethoxycarbonyl-3-(2'-propyl)-1,4-dithiacyclohept-2-ene-1,1,4,4-tetroxide By following substantially the procedure of Example 3, Step D, 2-ethoxycarbonyl-3-(2'-propyl)-1,4-dithiacyclohept-2-ene oxide (6.20 g.) yields 3.44 g. of 2-ethoxycarbonyl-3-(2'-propyl)-1,4-dithiacyclohept-2-ene-1,1,4,4-tetroxide, m.p. 114.5°–116.5° C.

Elemental analysis for $C_{11}H_{18}O_6S_2$; Calc.: C, 42.57; H, 5.85; S, 20.66; Found: C, 42.35; H, 5.95; S, 20.74.

What is claimed is:

1. A pharmaceutical composition useful in treating gastric ulcers which comprises an effective amount of a compound of the formula:

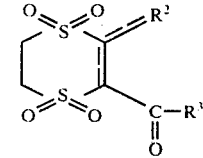

wherein $R^2$ is hydrogen, lower alkyl or cyano and $R^3$ is lower alkoxy, lower alkylamino or di-lower alkylamino in a pharmaceutically acceptable carrier.

2. A pharmaceutical composition useful in treating gastric ulcers which comprises an effective amount of 2-ethoxycarbonyl-5,6-dihydro-1,4-dithiin-4-oxide in a pharmaceutically acceptable carrier.

3. A pharmaceutical composition useful in treating gastric ulcers which comprises an effective amount of 2-ethoxycarbonyl-2-methyl-3-methylene-1,4-dithiane-1,1,4,4-tetroxide in a pharmaceutically acceptable carrier.

4. A pharmaceutical composition useful in treating gastric ulcers which comprises an effective amount of 3-ethoxycarbonyl-2-(2'-propyl)-5,6-dihydro-1,4-dithiin-1,1,4,4-tetroxide in a pharmaceutically acceptable carrier.

5. A pharmaceutical composition useful in treating gastric ulcers which comprises an effective amount of 3-ethoxycarbonyl-2-n-propyl-5,6-dihydro-1,4-dithiin-1,1,4,4-tetroxide in a pharmaceutically acceptable carrier.

6. A pharmaceutical composition useful in treating gastric ulcers which comprises an effective amount of 3-ethoxycarbonyl-2-(but-3'-enyl)-5,6-dihydro-1,4-dithiin-1,1,4,4-tetroxide in a pharmaceutically acceptable carrier.

7. A method for treating gastric ulcers which comprises administering to a person in need of such treatment an effective amount of a compound of the formula:

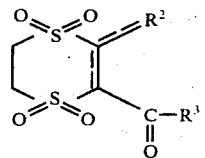

wherein $R^2$ is hydrogen, lower alkyl or cyano and $R^3$ is lower alkoxy, lower alkylamino or di-lower alkylamino.

8. A method for treating gastric ulcers which comprises administering to a person in need of such treatment an effective amount of 2-ethoxycarbonyl-5,6-dihydro-1,4-dithiin-4-oxide.

9. A method for treating gastric ulcers which comprises administering to a person in need of such treatment an effective amount of 2-ethoxycarbonyl-2-methyl-3-methylene-1,4-dithiane-1,1,4,4-tetroxide.

10. A method for treating gastric ulcers which comprises administering to a person in need of such treatment an effective amount of 3-ethoxycarbonyl-2-(2'-propyl)-5,6-dihydro-1,4-dithiin-1,1,4,4-tetroxide.

11. A method for treating gastric ulcers which comprises administering to a person in need of such treatment an effective amount of 3-ethoxycarbonyl-2-n-propyl-5,6-dihydro-1,4-dithiin-1,1,4,4-tetroxide.

12. A method for treating gastric ulcers which comprises administering to a person in need of such treatment an effective amount of 3-ethoxycarbonyl-2-(but-3'-enyl)-5,6-dihydro-1,4-dithiin-1,1,4,4-tetroxide.

* * * * *

UNITED STATES PATENT AND TRADEMARK OFFICE
CERTIFICATE OF CORRECTION

PATENT NO. : 4,109,006
DATED : August 22, 1978
INVENTOR(S) : R. C. Johnson & P. L. deBenneville (Case 1)

It is certified that error appears in the above-identified patent and that said Letters Patent are hereby corrected as shown below:

Col. 5, Line 33, delete "[1]polysulfonic acid".

Col. 6, Line 9, insert footnote "[1]polysulfonic acid".

Col. 8, line 42, "3-hexyloxycarbonyl-21-n-, etc."
   should read --3-hexyloxycarbonyl-2-n- --.

Col. 14, Line 2 "O" should read --O, 22.57--.

Col. 15, Line 68 "C,59.96" should read --C,59.56--.

Col. 16, Line 9 "S, 21.10" should read --S,21.20--.

Col. 17, Line 66, "clohept-2-end" should read --clohept-2-ene--.

Signed and Sealed this

Thirteenth Day of February 1979

[SEAL]

Attest:

RUTH C. MASON
Attesting Officer

DONALD W. BANNER
Commissioner of Patents and Trademarks